United States Patent [19]

Alderman

[11] 4,115,922
[45] Sep. 26, 1978

[54] DENTAL CROWN AND BRIDGE SHADING SYSTEM

[76] Inventor: C. Gale Alderman, 437 Donalyn La., Berwyn, Pa. 19312

[21] Appl. No.: 724,981

[22] Filed: Sep. 20, 1976

[51] Int. Cl.² ............................................. G09B 19/00
[52] U.S. Cl. ........................................ 32/71; 206/83; 32/8
[58] Field of Search .................. 32/71, 12, 8; 206/83; 264/19, 20

[56] References Cited

U.S. PATENT DOCUMENTS

| Re. 22,331 | 6/1943 | Myerson | 32/8 |
|---|---|---|---|
| 825,578 | 7/1906 | Browne | 32/71 |
| 2,756,504 | 7/1956 | Levine | 32/71 |
| 2,765,534 | 10/1956 | Bloom et al. | 32/71 |
| 2,805,478 | 9/1957 | Adams | 32/71 |
| 3,470,615 | 10/1969 | Petner | 32/12 |

FOREIGN PATENT DOCUMENTS 1,491,108  7/1969  Fed. Rep. of Germany .............. 32/71

OTHER PUBLICATIONS

"Matching Tooth Shades in Porcelain", by E. Bruce Clark, Copyright 1933, Published by The Dentist Supply Co. of N.Y.

Primary Examiner—Russell R. Kinsey
Assistant Examiner—John J. Wilson
Attorney, Agent, or Firm—Charles A. McClure

[57] ABSTRACT

A standardized system of color or shade selection and application is provided for crown and bridge prosthodontia, especially involving composite metal-ceramic crowns and bridges, using commercially available dental porcelains. A prosthodontic shade guide holds removable shade selectors to present separately distinct gingival and incisal shades of dental porcelain in accordance with their appearance on metal crowns and bridges. Each gingival shade selector comprises a thin opaque backing layer overlain by a thicker tapering body layer on a concave support, while each incisal shade selector comprises a thick tapering convex layer suitably supported. In the instance of a crown, the tooth is reduced dimensionally corresponding to the shade selector thicknesses (both gingival and incisal), and the crown is fabricated to a basic thickness to accommodate the respective layers. The crown is covered similarly to the shade selectors with such an opaque layer, then with such body layer, and finally such incisal layer is applied in desired depth to the incisal portion and is drawn down progressively thinner toward the gum line to duplicate the range of natural tooth color being matched.

4 Claims, 13 Drawing Figures

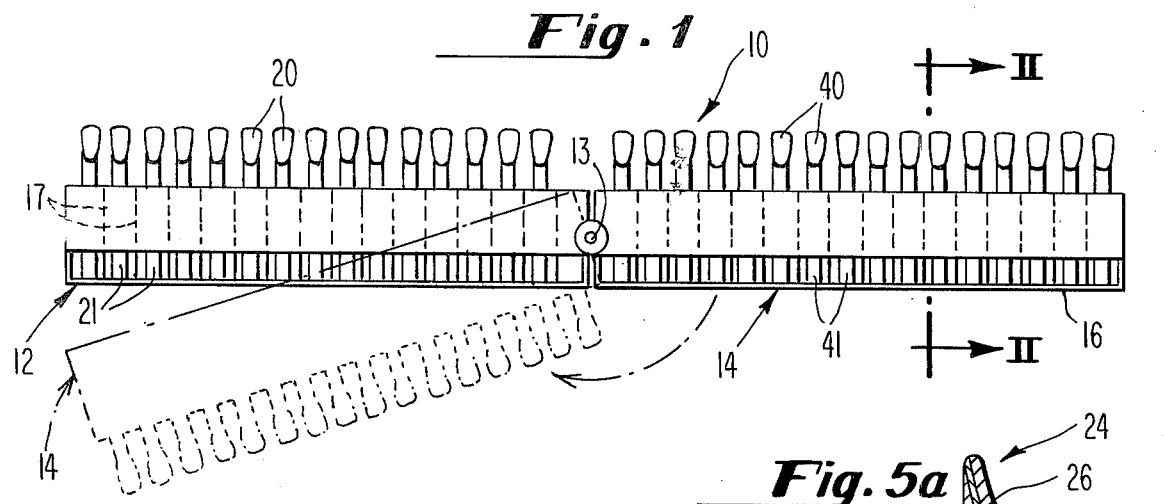
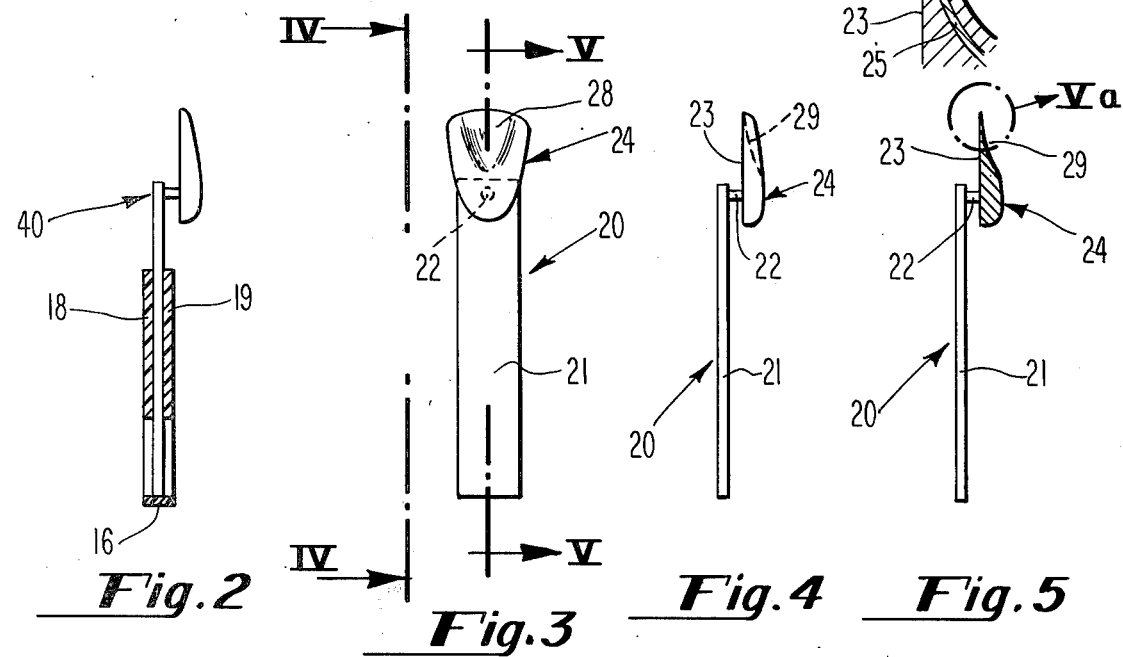
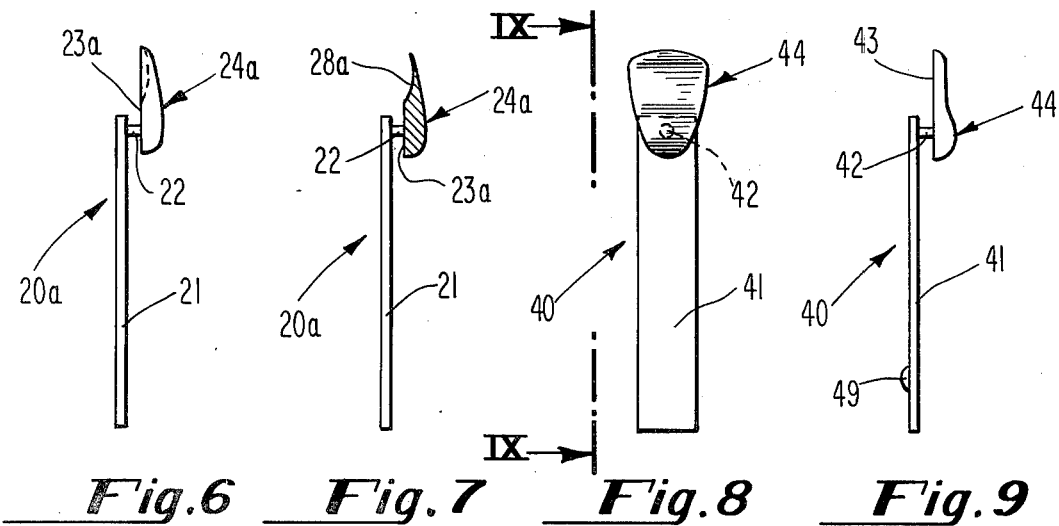

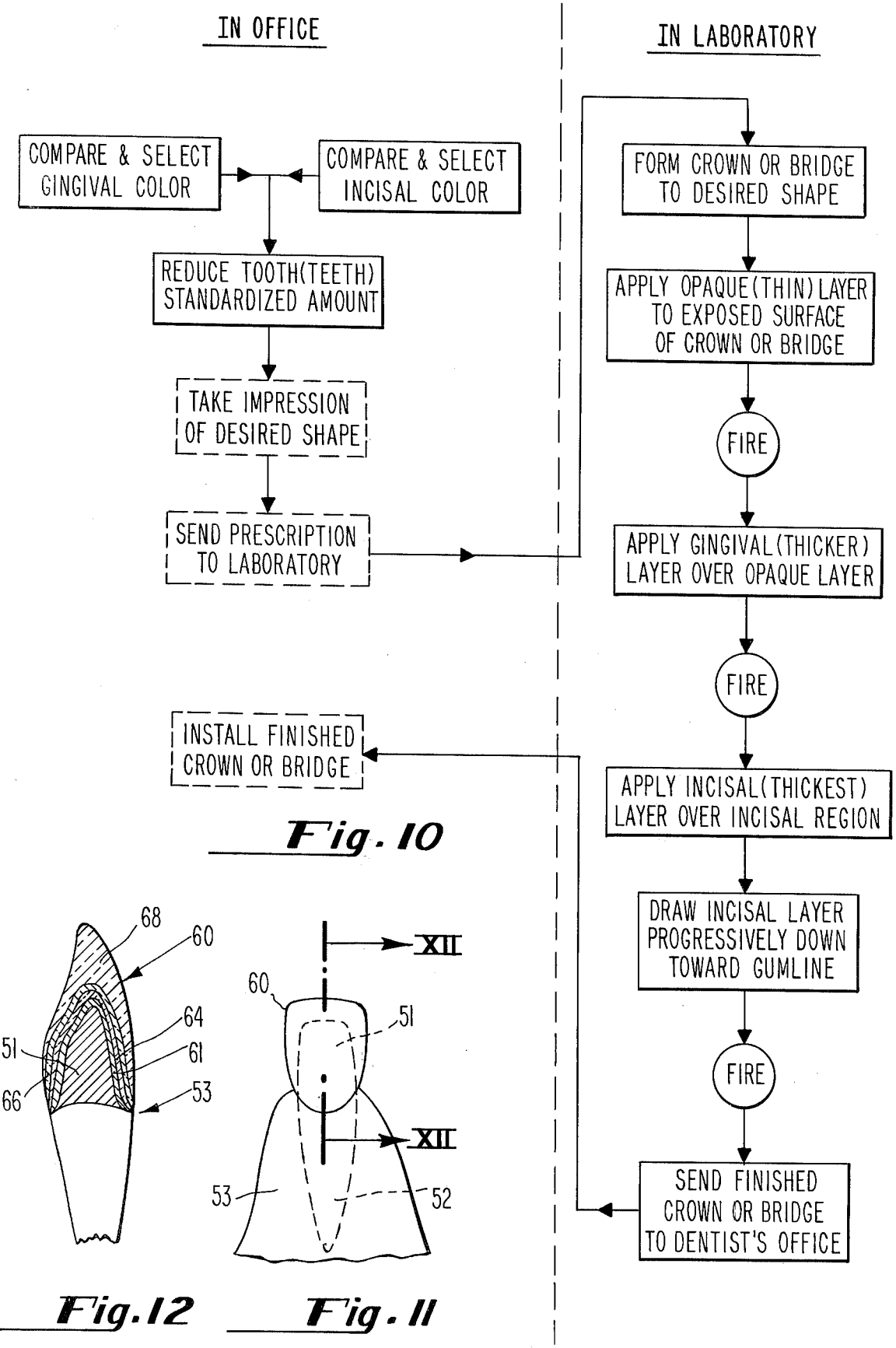

DENTAL CROWN AND BRIDGE SHADING SYSTEM

This invention relates to a standardized system of color or shade selection and application for crown and bridge prosthodontia, especially metal-ceramic crowns and bridges, using commerically available dental porcelains or like ceramic materials and features a crown-and-bridge prosthodontic shade guide with removable shade selectors for gingival shades and, separately, incisal shades.

Prosthodontic shade guides for use in matching dentures or replacement teeth to natural tooth color are available, and they also are commonly resorted to by dentists who desire to match a crown or bridge instead. Irrespective of the suitability of such shade guides for their original purpose, they are not at all suitable for use in the provision of crowns and bridges. The reason for their deficiency is that, whereas denture teeth resemble natural teeth in thickness and translucency, crowns and bridges usually have a metallic substructure and only a relatively thin coating of dental porcelain or the like. In addition, while conventional shade guides usually provide a range of gingival color or shading, they may fail to do so for the more prominent incisal region. Thus, the matching of crowns or bridges through the use of such guides is hardly feasible.

A primary object of the present invention is to standardize the color matching of dental crowns and bridges to natural teeth.

Another object of this invention is provision of a dental shade guide for use in matching crowns or bridges to natural teeth.

A further object of the invention is an improved stepwise method of coloring dental crowns and bridges facilitated by use of such a guide.

Yet another object is standardization of component materials and material thicknesses is such shade selectors, in such coloring method, and in such crowns and bridges themselves.

Other objects of the present invention, together with means and methods of attaining the various objects, will be apparent from the following description and the accompanying diagrams, which are presented by way of example rather than limitation.

FIG. 1 is a front elevation of a dental shade guide of the present invention, shown in an open position adapted to provide access to any of its removable shade selectors, with a partially closed position thereof being shown in broken lines;

FIG. 2 is a side sectional elevation of the shade guide, taken at II—II on FIG. 1.

FIG. 3 is a front elevation of a gingival shade selector of the same guide shown removed from the holder thereof;

FIG. 4 is a side elevation of the shade selector of FIG. 3, taken at IV—IV thereon;

FIG. 5 is a medial side sectional elevation of the same shade selector, taken at V—V on FIG. 3;

FIG. 5a is an enlarged detail view of an upper part of FIG. 5;

FIG. 6 is side elevation for an alternative embodiment of the shade selector of FIG. 3.

FIG. 7 is a medial side sectional elevation of the alternative gingival shade selector of FIG. 6, taken at VII—VII thereon;

FIG. 8 is a front elevation of an incisal shade selector shown removed from the holder of the guide shown in previous views;

FIG. 9 is a side elevation of shade selector of FIG. 8, taken at IX—IX thereon;

FIG. 10 is a schematic flow or block diagram of matching a dental crown or bridge to natural tooth color by this invention;

FIG. 11 is a front elevation, partly cut away, of a tooth fitted with a crown shaded according to this invention; and FIG. 12 is a side sectional elevation of the same tooth crown on an enlarged scale, taken at XII—XII on FIG. 11.

In general, the objects of the present invention are accomplished by means of a shade guide for metal-ceramic crowns and bridges comprising a holder, a plurality of gingival shade selectors held thereby and a separate plurality of incisal shade selectors held thereby. A gingival shade selector of this invention comprises a support and a shade button supported thereby, the shade button including an opaque backing layer and a thicker overlying body layer of given shade, and an incisal shade selector having a like support and a uniformly shaded button thereon. Further particulars of the guide and selector structure are set forth below.

Matching a dental crown or bridge to natural tooth color according to this invention is accomplished by using such a shade guide, described further below, to match a gingival shade selector to the gingival portion of the tooth and to match an incisal shade selector to the incisal portion of the tooth, applying an opaque backing layer to the crown or bridge, then applying a body layer in the selected shade over the backing layer, and finally applying an incisal layer in the selected shade to the incisal region and drawing it down progressively thinner toward the gum line to blend from the incisal to the gingival shade as in the natural tooth.

More specifically, the method of the present invention includes the steps of applying an opaque backing layer of dental porcelain or the like to the crown or bridge and firing it, then applying a body layer of dental porcelain in a selected gingival shade over the backing layer and firing the body layer, and finally applying an incisal layer of dental porcelain in a selected shade to the incisal region and drawing it down progressively thinner toward the gum line to blend from the incisal to the gingival shade, as in the natural tooth, and firing it.

FIGS. 1 and 2 show a shade guide according to this invention viewed from the front and the side (in section). Shade guide 10 comprises left and right halves 12 and 14 pivoted intermediately on pin 13 having its pivot axis perpendicular to the plane of the guide. This enables the respective halves to be pivoted from the illustrated open position to a closed position in which one half overlies the other, as suggested by the partially closed position shown in broken lines in FIG. 1. Each half of the guide comprises numerous parallel cylindrical compartments, each adapted to receive and to retain one of equally numerous shade selectors.

As shown, left half 12 of the guide holds gingival shade selectors 20, and right half 14 holds incisal shade selectors 40. The holder portions of the guide conveniently comprise rear band 18 overlain by upper front band 19 spaced above the bottom but contiguous with the rear via vertical walls 17 between successive compartments formed by the bands. Bottom strip 16 joins the side edges and the rear band. Front band 19 conveniently carries alphanumeric designations (not shown) of the respective gingival and incisal colors or shades overlying the respective compartments. Of course, the shade selector for each such compartment corresponds thereto in designation.

FIGS. 3, 4, and 5 show a first embodiment of gingival shade selector 20 from the front, side, and in medial vertical section. Stemlike handle 21 carries gingival shade button 24, which conveniently has a generally toothlike outline as shown from the front in FIG. 2. The button, composed of dental porcelain or the like, has full-length vertical back 23 and is secured to the handle by horizontal pin 22 therebetween as shown in the side view of FIG. 4, the button tapers from a relatively thick base to a thin top edge portion, and as further shown in the sectional view of FIG. 5 the tapering portion is concave toward the face of the button so that the gingival color layer of dental porcelain or the like occupies a dished portion 29 of the button face. Although not visible in the latter view, gingival color layer 26 is underlain by a thinner backing layer 25 of opaque dental porcelain or the like, as shown in detail view in FIG. 5a.

FIGS. 6 and 7 show from the side and in like vertical section alternative embodiment of gingival shade selector 20a. Parts here corresponding to those of the first embodiment are designated by the same reference numeral with addition of the letter: a, whether or not the respective parts differ or are entirely alike. Noticeably different here is that vertical back 23a is shorter to accommodate concave tapering 28a of the rear face of button 24a. The gingival color layer and underlying opaque backing layer (not shown) are located on the opposite portion of the front face of the button, which is not dished in this embodiment.

FIGS. 8 and 9 show from the front and sides, respectively, incisal shade selector 40. Stemlike handle 41 carries incisal shade button 44, which has vertical back 43 secured to the handle by pin 42. This button also is generally toothlike in outline as viewed from the front. As viewed from the side, it tapers convexly to a relatively thin portion at its top edge, which is remote from its junction to the handle. Unlike the gingival buttons, this incisal button is composed uniformly of a shade of dental porcelain or the like and does not have any dished face or added layers of different shades thereon. Protrusion 49 from the rear wall of the handle of this selector near the bottom is adapted to fit into a corresponding recess (not shown) in the front surface of the rear wall of the holder to retain the selector frictionally against being dislodged accidentally but not so securely as to defeat intended manual removal of such selector. All the selectors may carry similar protrusions, which may be relocated (together with the holder wall recesses) further up the handle and on the inside surface of either the front or rear wall of the holder.

The alphanumeric designations of the respective shades may be displayed conveniently on the stemlike handles of the shade selectors as well as on the upper band of the holder. The shades and their designations are arbitrary, being composable from commercially available dental porcelains and coloring materials. The designations may include letters corresponding to various colors, such as Y (yellow), O (orange), B (blue), V (violet), and G (grey), and numbers designating various hues and/or saturations (often called "chroma" in dental work). Brilliance or brightness (sometimes called "value") depends in substantial part upon presence or absence of adjacent opacity in a crown or bridge, and the shades represented should be inherently bright enough rather than weak tones and can be made less bright, if desired, by judicious addition of violet. More saturated colors can be produced by addition of both blue and orange to form grey complements. The designations are omitted from the drawings.

Inasmuch as the available thickness for a finished crown or bridge usually is limited to a couple millimeters, and thickness markedly affects apparent colors or shades, the shade selector buttons of this invention are standardized dimensionally to approximate closely corresponding dimensions of a finished crown, for example. The customary metal thimble substructure of a crown or bridge is normally about half a millimeter thick, leaving at most only about one and a half millimeters of thickness available for the coloring or shading materials. In contrast, a prosthodontic guide for dentures may provide transulucent (non-opaque) buttons half a centimeter thick because the denture teeth will be that thick and will be mounted on translucent plastic material instead of on a non-translucent (opaque) ceramic-metal material.

Thus, the relatively simple incisal shade buttons according to the present invention will be about one millimeter thick at their shade-comparing edge remote from the junction to the handle, where the button is preferably about twice as thick. The more complex gingival button tapers to about a half millimeter thick at the shade-selection region, where the opaque backing layer approximates two-tenths of a millimeter in thickness, and the overlying gingival body layer is about half again as thick. The support porcelain portion of the gingival button is as thick as the incisal button at the side edges and base but is minimally thin where the dished gingivally colored portion of its face meets that top edge.

FIG. 10 shows the steps performed in matching a crown or bridge to natural tooth color according to this invention, as by using the materials already described. The steps performed by the dentist in the office are at the left, while those performed in the laboratory (usually by a technician) are at the right. The conventional steps of molding the shape desired (as by an impression made in the patient's mouth), forming the crown or bridge to the desired shape, and finally installing the finished crown or bridge are enclosed in broken lines and not mentioned further, while the novel steps are enclosed in solid lines, and are described in more detail below. Thus, after the steps of comparing and selecting a gingival color and comparing and selecting an incisal color, the first novel step is to reduce the tooth (or teeth) appropriately in dimensions as already mentioned, all done in the office. After transmittal of the pertinent information to the laboratory, and formation of the desired shape there, the next step is to apply a thin opaque layer of dental porcelain or the like to the exposed surface of the crown or bridge, which is then fired. Then come the steps of applying the selected gingival color in a thicker layer over the opaque layer, and firing again. Finally come the steps of applying the selected incisal color as the thickest layer on the incisal region of the crown or bridge, drawing it down progressively thinner toward the gum line, and firing again. The time consumed in the three separate firings is made up by reduction in the time required for manual adjustment in layer thickness and contouring.

FIGS. 11 and 12 show in front elevation, partly cut away, and in enlarged transverse section, respectively, a tooth fitted with a crown shaded according to this invention. Tooth body 51 is shown protruding beyond gum 53, and root portion 52 thereof below the gum line (both in broken lines). Fitting over the tooth body is crown 60, which has metallic "thimble" 61 covered by various porcelain layers. Opaque layer 64 covers the outer or orginally exposed surface of the thimble and is covered in turn by body layer 66 of gingival shading, the respective layers being about 0.2 and 0.3 millimeter thick as best shown in the sectional view. Outermost layer 68, of incisal shade, is thickest and is drawn down progressively thinner toward the gum line.

It will be understood, of course, that young people usually have translucent incisal edges on their teeth whereas most elderly people have little or none, as a result of a lifetime of abrasion. Similarly, the gingival color for a young person can be expected to be lighter yellow, as well as more translucent, than the darker yellow-orange and less translucent color of an older person's tooth. However, there are many individual differences, and the eye is so apt to detect non-matching regions, that the standarized procedure of this invention provides what is needed to eliminate the ambiguity of outcome that has characterized previous approaches to this art.

No special materials are required. Conventional dental ceramic compositions or porcelains now available are suitable for forming the various layers, although considerable judgment is essential to producing a satisfying stepwise range of shades for greatest convenience in use. Deviations in layer thickness such as otherwise would introduce uncontrolled color variations, owing to disproportionate preponderance of incisal color or gingival body color (and related chroma variations) are eliminated by the standardization provided by this invention. The precise make-up of mixtures to produce an optimum range of shades is not part of the present invention, inasmuch as a wide variety of combinations may be provided that can be used. The holder may be made of any convenient plastic or of metal or wood. The non-ceramic parts of the shade selectors may be similarly composed, although economy suggests plastic handles joined to the shade buttons by metal pins.

Notwithstanding concentration in description and illustration upon a single embodiment, except in the instance of the gingival shade selector buttons, other modifications may be made, as by adding, combining, or subdividing parts or steps, or substituting equivalents, while retaining advantages and benefits of this invention, which itself is defined in the following claims.

I claim:

1. In a shade guide for dental crowns and bridges, the combination of a holder, a plurality of gingival shade selectors held thereby and a separate plurality of incisal shade selectors held thereby, each such selector comprising a shade button having an opaque backing layer, with each shade button of the gingival shade selectors having a concave portion tapering to a relatively thin edge, and each shade button of the incisal shade selectors having a corresponding edge portion that is convex and relatively thicker than that of the gingival shade button.

2. Dental shade guide according to claim 1, wherein the individual shade selectors are held removably by the holder.

3. Dental shade guide according to claim 1, wherein the holder has pivot means enabling it to be folded between its ends to juxtapose the respective ends to one another.

4. Dental shade guide according to claim 1, wherein the holder has a plurality of slots to receive the individual shade selectors, each of which includes a stemlike handle adapted to fit removably within such a slot.

* * * * *